United States Patent
Sauer et al.

(10) Patent No.: US 6,245,032 B1
(45) Date of Patent: Jun. 12, 2001

(54) JET NOZZLE FOR AN ORAL IRRIGATOR

(75) Inventors: Michael Sauer, Bad Camberg; Norbert Schaefer, Frankfurt; Michael Stolper, Eschborn, all of (DE)

(73) Assignee: Braun GmbH, Frankfurt am Main (DE)

( * ) Notice: Subject to any disclaimer, the term of this patent is extended or adjusted under 35 U.S.C. 154(b) by 0 days.

(21) Appl. No.: 08/958,355

(22) Filed: Oct. 27, 1997

(30) Foreign Application Priority Data

Nov. 6, 1996 (DE) .............................. 196 45 644

(51) Int. Cl.$^7$ ................................... A61H 13/00
(52) U.S. Cl. ..................... 601/162; 433/80; 601/163; 601/164; 601/165
(58) Field of Search ................ 433/80; 601/162, 601/163, 164, 165

(56) References Cited

U.S. PATENT DOCUMENTS

| | | | | |
|---|---|---|---|---|
| 2,516,195 | * | 7/1950 | Finton | 601/163 |
| 3,739,983 | | 6/1973 | Jousson | 601/162 |
| 4,671,259 | * | 6/1987 | Kirchner | 601/162 |
| 4,672,953 | * | 6/1987 | DiVito | 601/162 |
| 5,265,806 | * | 11/1993 | Ferrarini | 239/251 |
| 5,616,028 | * | 4/1997 | Hafele et al. | 433/80 |

FOREIGN PATENT DOCUMENTS

| | | |
|---|---|---|
| 42 39 542 A1 | 9/1993 | (DE) . |
| 0 245 628 | 11/1987 | (EP) . |
| 0 175 881 | 12/1990 | (EP) . |
| 0 542 698 | 5/1993 | (EP) . |
| 0 688 542 | 12/1995 | (EP) . |
| 2 475 939 | 8/1981 | (FR) . |
| 96/25121 | 8/1996 | (WO) . |

\* cited by examiner

*Primary Examiner*—John J. Wilson
(74) *Attorney, Agent, or Firm*—Fish & Richardson P.C.

(57) ABSTRACT

The invention is directed to a jet nozzle (1) for a handle section of an oral irrigator. The jet nozzle (1) is provided with a nozzle head (2) having a discharge port (18) from which a liquid in the form of a single jet is dischargeable. The nozzle head (2) receives therein an impeller (6) rotary about an axis of rotation (4). The impeller (6) includes a bore (15) disposed at an angle (22) to the axis of rotation (4). The bore (15) is intended to direct the liquid to the discharge port (18). In operation, the impeller (6) executes a rotary motion about the axis of rotation (4). This creates a single jet exiting from the discharge port (18) and revolving on the surface of a cone. With this revolving single jet, a superior cleaning effect is accomplished in the cleansing and care of teeth and gums.

22 Claims, 2 Drawing Sheets

JET NOZZLE FOR AN ORAL IRRIGATOR

Figure 1:
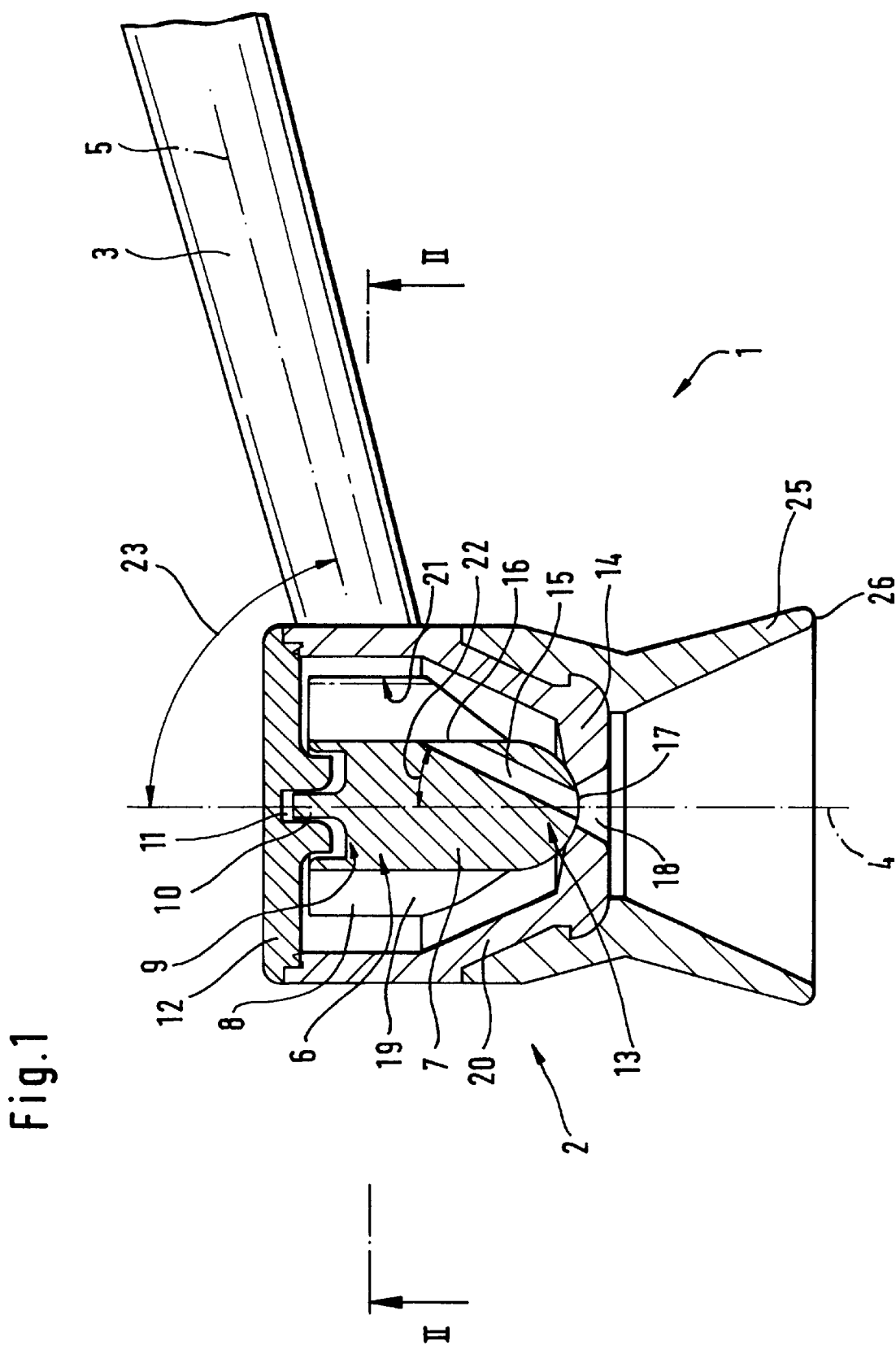

This invention relates to a jet nozzle for a device for the cleaning and care of teeth and gums, in particular for a handle section of an oral irrigator, with a nozzle head having a discharge port from which a liquid in the form of a single jet is dischargeable.

A jet nozzle of this type is known from European Patent Specification No. EP 0 175 881 B2. This specification describes an electrically powered oral irrigator for oral and dental hygiene which includes a handle section to which a jet nozzle is attachable. The jet nozzle is provided with a nozzle head having a discharge port from which a single jet is dischargeable. Further, the nozzle head accommodates means for selectively enabling the single jet to be fanned out, resulting in a multiple jet. With the oral irrigator in operation, water is pumped to the jet nozzle and thus to the nozzle head. The single or multiple jet produced enables a user of the oral irrigator to care for and cleanse the oral cavity and in particular teeth and gums.

It is an object of the present invention to further develop the known jet nozzle with a view to improving the care and cleaning effect.

According to the present invention, this object is accomplished in that the nozzle head receives therein an impeller rotary about an axis of rotation, that the impeller includes a bore disposed at an angle to the axis of rotation, and that the bore is intended to direct the liquid to the discharge port.

In operation of the device of the present invention, the impeller is set in rotation about the axis of rotation by the liquid pumped to the nozzle head. This also involves a rotation of the bore extending within the impeller equally about the axis of rotation. By arranging the bore at an angle to the axis of rotation, the bore moves on the surface of a cone. In consequence, the single jet exiting from the bore revolves likewise on the surface of a cone. The result thereby achieved is that the liquid pumped through the bore, upon exiting from the bore, is distributed relatively uniformly on the surface of the cone as a revolving single jet.

It will thus be seen that, to obtain a multiple jet, the single jet, rather than being fanned out in some way, is maintained as a single jet. To produce the effect of a multiple jet, the single jet is set in rotation, that is, it is subjected to continuous deflection.

This has the advantage that the single jet does not become diffuse by fanning out which diminishes the cleaning effect of the single jet, but rather, the full cleaning effect of the concentrated single jet is maintained. The deflection of the single jet by rotation affords the added advantages of a multiple jet, which include in particular a simpler and more comprehensive cleansing of individual teeth by the user. Overall, the present invention makes a jet nozzle available in which the advantages of a single jet, in particular its superior cleaning action, also apply fully to a multiple jet.

In a particularly advantageous further development of the present invention, the angle has a value in the range from about 10 degrees to about 40 degrees, preferably of about 25 degrees. With the angle between the axis of rotation and the bore having such values, an opening cone can be produced. Further, the cone on which the single jet revolves can be adjusted to a size corresponding approximately to the size of a single tooth. A particularly good and thorough tooth cleaning action is thereby accomplished. At the same time, manipulation of the device of the present invention by its user is facilitated.

In an advantageous configuration of the present invention, the impeller includes a core piece as well as a plurality of approximately radially outwardly extending blades, the bore extending in the core piece, and the inlet orifice of the bore being arranged between two blades. This represents a particularly simple and hence economical configuration, in particular in terms of the manufacture of the jet nozzle of the present invention. Particularly suitably, the impeller is fabricated from a plastic material using in particular an injection molding method.

In a further advantageous configuration of the present invention, the discharge port of the nozzle head is arranged coaxially with the axis of rotation, and the outlet orifice of the bore is equally arranged approximately coaxially with the axis of rotation, said outlet orifice of the bore and said discharge port of the nozzle head being arranged adjacent to one another. The outlet orifice of the bore thus forms the upper part or the tip of the cone on which the single jet revolves. The downstream discharge port of the nozzle head is configured such that the revolving single jet exiting from the bore is not impeded by the discharge port.

In another advantageous aspect of the present invention, a supply tube is provided on which the nozzle head is mounted, the longitudinal axis of the supply tube and the axis of rotation of the impeller being arranged at a relative distance. This distance ensures that the liquid fed through the supply tube to the nozzle head does not impinge upon the impeller centrally, but eccentrically. This means that the liquid strikes the blades of the impeller, thus setting the impeller in rotation. By reason of the relative distance of the longitudinal axis of the supply tube to the axis of rotation of the impeller, a cross afflux is accomplished in a particularly simple and yet effective manner, causing rotation of the impeller.

In an advantageous further development of the present invention, the longitudinal axis of the supply tube and the axis of rotation of the impeller are disposed at a relative angle in the range from about 60 degrees to about 90 degrees, preferably of about 75 degrees. This results in an inclined position of the supply tube in the direction of the discharge port of the nozzle head. The flow conditions in the interior of the nozzle head are thereby improved, so that the deflection of the single jet within the nozzle head results only in a negligible reduction of the flow rate of the single jet. The cleaning effect of the single jet is not diminished by the rotary motion.

In an advantageous configuration of the present invention, the nozzle head is provided with a spacer which surrounds the discharge port of the nozzle head preferably conically, is arranged approximately coaxially with the axis of rotation, and extends in the direction of the liquid exiting from the discharge port. The user may engage the nozzle head with its spacer directly against the tooth to be cleaned. The spacer ensures that the single jet exiting from the nozzle head impinges substantially only upon the tooth to be cleaned, excluding adjacent teeth. The spacer further avoids any accidental discharge of splash water from the oral cavity which may cause undesired soiling. In this regard, the spacer acts as a splash guard. Further, the length of the spacer in the direction of the liquid exiting from the discharge port may be selected such that the cone formed by the revolving single jet has just about the size of the tooth to be cleaned. This further adds to improving the tooth cleaning action, in addition to further simplifying the operation of the device of the present invention for its user.

In an advantageous further development of the present invention, the spacer includes at least one notch. This notch enables the liquid exiting from the nozzle head to drain off also in cases where the spacer is directly engaged against a tooth.

Moreover, the spacer may advantageously include bristles or bristle tufts, or it may be integrally formed with the nozzle head.

Further features, advantages and application possibilities of the present invention will become apparent from the subsequent description of embodiments illustrated in more detail in the accompanying drawing. It will be understood that any single feature and any combination of single features described and/or represented by illustration form the subject-matter of the present invention, irrespective of their summary in the claims and their back-reference. In the drawings, FIG. 1 is a schematic sectional view of an embodiment of a jet nozzle constructed in accordance with the present invention, taken along the plane I—I of FIG. 2; and FIG. 2 is a schematic sectional view of the jet nozzle of FIG. 1, taken along the plane II—II of FIG. 1.

Figure 2:
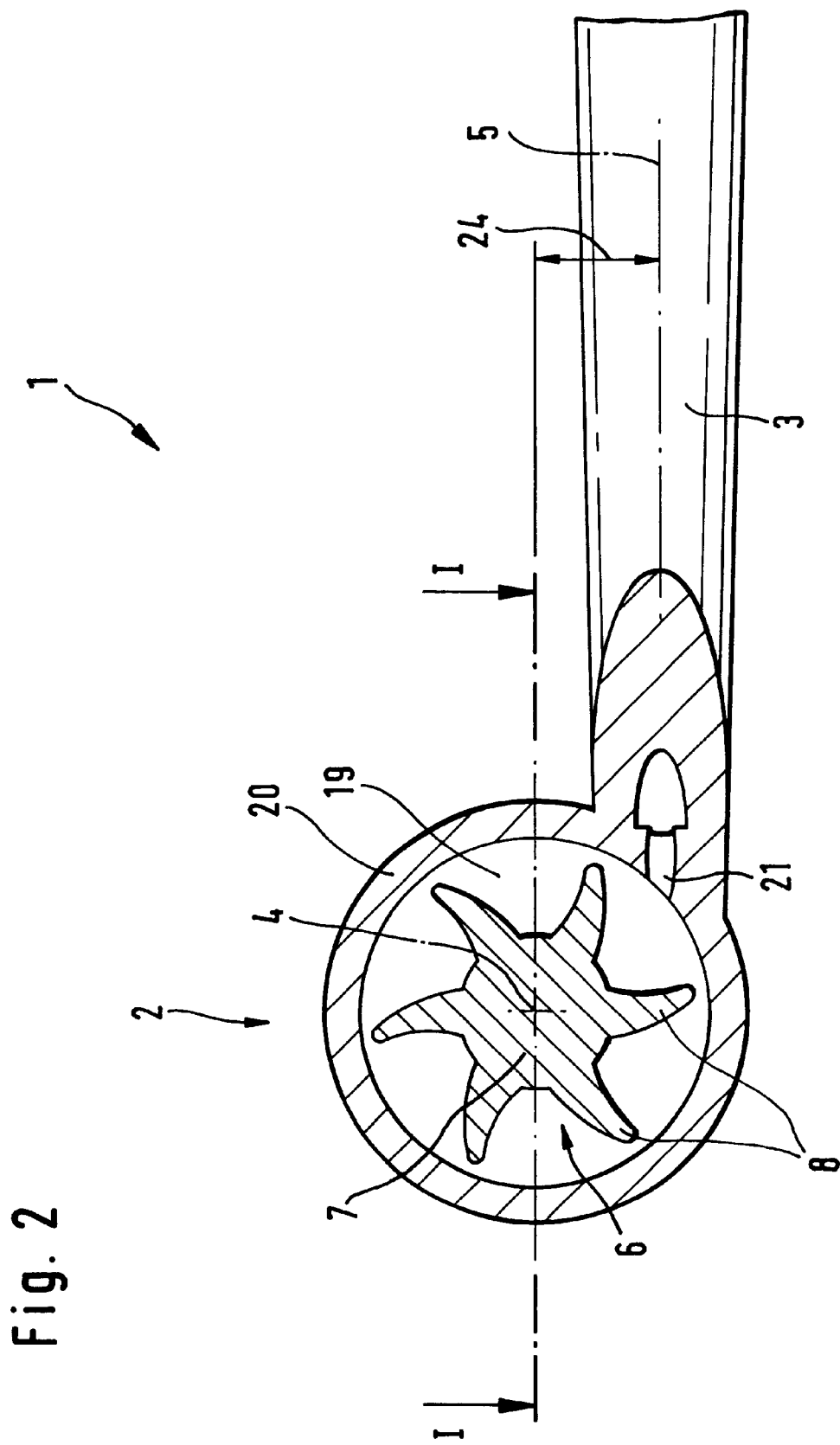

FIGS. 1 and 2 illustrate a jet nozzle 1 for an oral irrigator. The jet nozzle 1 is demountably attachable to a handle section coupled through a hose to the oral irrigator. The oral irrigator comprises a liquid reservoir fillable with water by a user. Received in the housing of the oral irrigator is a pump driven by an electric motor for delivering the water from the liquid reservoir through the hose to the handle section and thus onward to the jet nozzle 1. In operation of the oral irrigator, the water jet produced by the jet nozzle can be used for the care and cleaning of the user's teeth and gums.

The jet nozzle 1 includes a nozzle head 2 connected to a supply tube 3. The nozzle head 2 is configured so as to be approximately symmetrical about an axis of rotation 4, and the supply tube 3 extends in the direction of a longitudinal axis 5.

Accommodated in the interior of the nozzle head 2 is an impeller 6 having a core piece 7 and six blades 8. The impeller 6 is of an essentially rotationally symmetrical configuration and is arranged coaxially with the axis of rotation 4.

The core piece 7 is approximately cylindrical, having at its one end 9 a pin-shaped projection 10 engaging in a mating recess 11 in the rear wall 12 of the nozzle head 2. The projection 10 and the recess 11 are arranged coaxially with the axis of rotation 4. The other end 13 of the core piece 7 is of an approximately hemispherical shape, abutting the front wall 14 of the nozzle head 2 such that the core piece 7 as a whole is located coaxially with the axis of rotation 4 and rotatable about the axis of rotation 4.

A bore 15 extends through the core piece 7 of the impeller 6. The bore 15 extends in a straight line from an inlet orifice 16 to an outlet orifice 17. The inlet orifice 16 is located on the outer surface of the core piece 7 approximately midway between the two ends 9, 13 of the core piece 7. The outlet orifice 17 is located in the area of the apex of the hemispherical end 13 and is thus arranged approximately coaxially with the axis of rotation 4.

Immediately adjacent to the outlet orifice 17 of the bore 15, the nozzle head 2 has in its front wall 14 a discharge port 18 which is arranged coaxially with the axis of rotation 4 and has the hemispherical end 13 of the core piece 7 in engagement with its edge.

The six blades 8 of the impeller 6 are equidistantly spaced on the circumference of the core piece 7, extending approximately radially outwardly from the core piece 7. The inlet orifice 16 of the bore 15 is located between two blades 8. The impeller 6 is capable of rotation in an inner chamber 19 of the nozzle head 2, said inner chamber 19 being bounded by the rear wall 12, the front wall 14 and an approximately cylindrical side wall 20. Further, the inner chamber 19 is connected through an inlet port 21 with the supply tube 3.

The bore 15 and the axis of rotation 4 are disposed at a relative angle 22. The bore 15 is thus inclined relative to the axis of rotation 4. The angle 22 has a value in the range from about 10 degrees to about 40 degrees. The angle 22 preferably has a value of about 25 degrees. The angle 22 becomes apparent particularly from FIG. 1.

The longitudinal axis 5 of the supply tube 3 and the axis of rotation 4 are disposed at a relative angle 23. The supply tube 3 is thus inclined towards the axis of rotation 4. The angle 23 has a value in the range from about 60 degrees to about 90 degrees. The angle 23 preferably has a value of about 75 degrees. The angle 23 becomes apparent particularly from FIG. 1.

The longitudinal axis 5 of the supply tube 3 and the axis of rotation 4 are further arranged at a relative distance 24. The distance 24 is selected such that the water entering through the inlet port 21 into the inner chamber 19 of the nozzle head 2 impinges upon the blades 8 of the impeller 6. The distance 24 becomes apparent particularly from FIG. 2.

Releasably attached to the nozzle head 2 is a spacer 25. The spacer 25 is of an approximately conical configuration, surrounding the discharge port 18 of the nozzle head 2. Further, the spacer 25 is arranged approximately coaxially with the axis of rotation 4, extending in the direction of the liquid exiting from the discharge port 18. The spacer 25 may have notches or the like on its free edge 26.

With the oral irrigator in operation, the water is pumped from the liquid reservoir to the jet nozzle 1. There the water arriving from the supply tube 3 enters the inlet port 21, reaching the inner chamber 19 of the nozzle head 2. By virtue of the relative distance 24 of the longitudinal axis 5 of the supply tube 3 to the axis of rotation 4 of the impeller 6, the water strikes the blades 8 of the impeller 6. This cross afflux acts to set the impeller 6 in rotation about the axis of rotation 4.

The water is pumped from the inner chamber 19 of the nozzle head 2 through the inlet orifice 16 into the bore 15 of the core piece 7. The water is fed through the bore 15, reaching the outlet orifice 17. There the water exits from the nozzle head 2 through the discharge port 18 arranged directly downstream thereof. As this occurs, the engagement of the hemispherical end 13 of the core piece 7 with the front wall 14 of the nozzle head 2 ensures that the water is allowed to exit from the nozzle head 2 essentially only through the bore 15.

With the impeller 6 rotating, the bore 15 is likewise set in rotation about the axis of rotation 4. As a result, the water passing through the bore 15 performs equally a rotary motion. As the water exits from the outlet orifice 17, it thus experiences a continuous change in direction, so that the single water jet expelled from the discharge port 18 revolves on the surface of a cone. Accordingly, the water jet is continuously deflected by the bore 15, such as to execute a rotary motion forming the referenced cone. In this process, the water jet forms an opening cone, with the outlet orifice 17 of the bore 15 defining the upper area or tip of the cone. Further, the angle 22 between the bore 15 and the axis of rotation 4 defines the opening angle of the cone.

The conical shape of the spacer 25 is selected such that the opening cone formed by the water jet does not strike the spacer 25. Accordingly, the selected opening angle of the spacer 25 is equal to or slightly larger than the opening angle of the water jet exiting from the discharge port 18. The length of the spacer 25 in the direction of the exiting water is selected such that the size of the cone formed by the water jet corresponds approximately to the size of a tooth.

What is claimed is:

1. A jet nozzle for a device for cleaning and care of teeth and gums, the jet nozzle comprising:

a nozzle head having a discharge port from which a liquid in the form of a single jet is dischargeable; and an impeller within the nozzle head and rotary about an axis of rotation, said impeller including a one-piece rotor body made of a plastic material and having only a single bore passing therethrough and disposed at an angle to the axis of rotation, said bore being aligned with and terminating at the discharge port and defining a passage through which the liquid flows during use to the discharge port, wherein said rotor body has elongate sidewalls and a front end wall, wherein the front end wall bears against an inside surface of the nozzle head in the vicinity of the discharge port.

2. The jet nozzle according to claim 1, wherein the angle has a value in the range from about 10 degrees to about 40 degrees.

3. The jet nozzle according to claim 2, wherein the angle has a value of about 25 degrees.

4. The jet nozzle according to claim 1, wherein the impeller further includes a a plurality of approximately radially outwardly extending blades on the rotor body, and wherein the bore extends through the rotor body, and wherein the bore has an inlet orifice arranged between two neighboring blades of said plurality of blades.

5. The jet nozzle according to claim 1 wherein the nozzle head has a discharge port arranged coaxially with the axis of rotation, wherein the bore has an outlet orifice arranged approximately coaxially with the axis of rotation, and wherein the outlet orifice of the bore and the discharge port of the nozzle head are arranged adjacent to one another.

6. The jet nozzle according to claim 1, further comprising a supply tube on which the nozzle head is mounted, wherein the supply tube has a longitudinal axis that is offset a relative distance from the axis of rotation of the impeller.

7. The jet nozzle according to claim 5, wherein the longitudinal axis of the supply tube and the axis of rotation of the impeller are disposed at a relative angle to each other, that relative angle being in the range from about 60 degrees to about 90 degrees.

8. The jet nozzle according to claim 7, wherein the relative angle is about 75 degrees.

9. The jet nozzle according to claim 1, wherein the nozzle head is provided with a spacer which surrounds the discharge port of the nozzle head, is arranged approximately coaxially with the axis of rotation, and extends in the direction in which the liquid exits from the discharge port during operation.

10. The jet nozzle according to claim 9, wherein the spacer includes at least one notch.

11. The jet nozzle according to claim 9, wherein the spacer comprises a ring of teeth-cleaning bristles.

12. The jet nozzle according to claim 9, wherein the spacer is an integrally formed extension of the nozzle head.

13. The jet nozzle according to claim 9, wherein the spacer comprises a ring of teeth-cleaning bristle tufts.

14. The jet nozzle according to claim 9, wherein the spacer conically surrounds the discharge port.

15. The jet nozzle according to claim 1, wherein the one-piece rotor body is made of a molded plastic material.

16. The jet nozzle according to claim 1, wherein the impeller includes pin-shaped element extending out of a back end of the rotor body.

17. The jet nozzle according to claim 16, wherein the rotor body includes an integrally-molded pin-shaped projection which is the pin-shaped element.

18. The jet nozzle according to claim 1, wherein the rotor body has a rotationally symmetric body shape.

19. The jet nozzle according to claim 18, wherein the rotor body is approximately cylindrical in shape with a circular cross-section and wherein the front end wall has a hemispherical shape.

20. A jet nozzle for a device for cleaning and care of teeth and gums, the jet nozzle comprising:

a nozzle head having a discharge port from which a liquid in the form of a single jet is dischargeable; and an impeller within the nozzle head and rotary about an axis of rotation, said impeller including a bore disposed at an angle to the axis of rotation, and said bore aligned with and intended to direct the liquid to the discharge port, wherein the nozzle head is provided with a ring of teeth-cleaning bristles which surrounds the discharge port of the nozzle head, is arranged approximately coaxially with the axis of rotation, and extends in the direction in which the liquid exits from the discharge port during operation.

21. An oral irrigator for the cleaning and care of teeth and gums, said oral irrigator comprising:

a jet nozzle according to claims 1 or 20; and a handle section to which the jet nozzle is attached.

22. The oral irrigator according to claim 21, wherein the jet nozzle is separable from the handle section.

* * * * *